United States Patent [19]

Baldwin

[11] Patent Number: 4,568,159

[45] Date of Patent: Feb. 4, 1986

[54] CCD HEAD AND EYE POSITION INDICATOR

[75] Inventor: Dorothy M. Baldwin, Lake Monroe, Fla.

[73] Assignee: The United States of America as represented by the Secretary of the Navy, Washington, D.C.

[21] Appl. No.: 444,639

[22] Filed: Nov. 26, 1982

[51] Int. Cl.[4] .............................................. A61B 3/14
[52] U.S. Cl. .................................................... 351/210
[58] Field of Search ................. 351/209, 210; 350/322

[56] References Cited

U.S. PATENT DOCUMENTS 3,473,868 10/1969 Young et al. ..................... 351/210
3,542,457 11/1970 Balding et al. .................... 351/210
4,075,657 2/1978 Weinblatt ............................ 351/210

Primary Examiner—Rodney B. Bovernick
Assistant Examiner—Paul M. Dzierzynski
Attorney, Agent, or Firm—Robert F. Beers; Robert W. Adams

[57] ABSTRACT

A head and eye tracking apparatus utilizes a plurality of coded IR emitters, mounted in a reflective surface, as a reference base. A reference lens aligned with the user's head references a limited number of the emitters within its field of view and transmits the image to a fiber optic bundle. Simultaneously, an IR reflection from the user's eye is superimposed on the image and transferred via the fiber optic bundle. A CCD array detects the IR transmission and provides a high speed read-out to a computer which can determine head and eye positions from the geometry of the emitters referenced by the lens.

7 Claims, 1 Drawing Figure

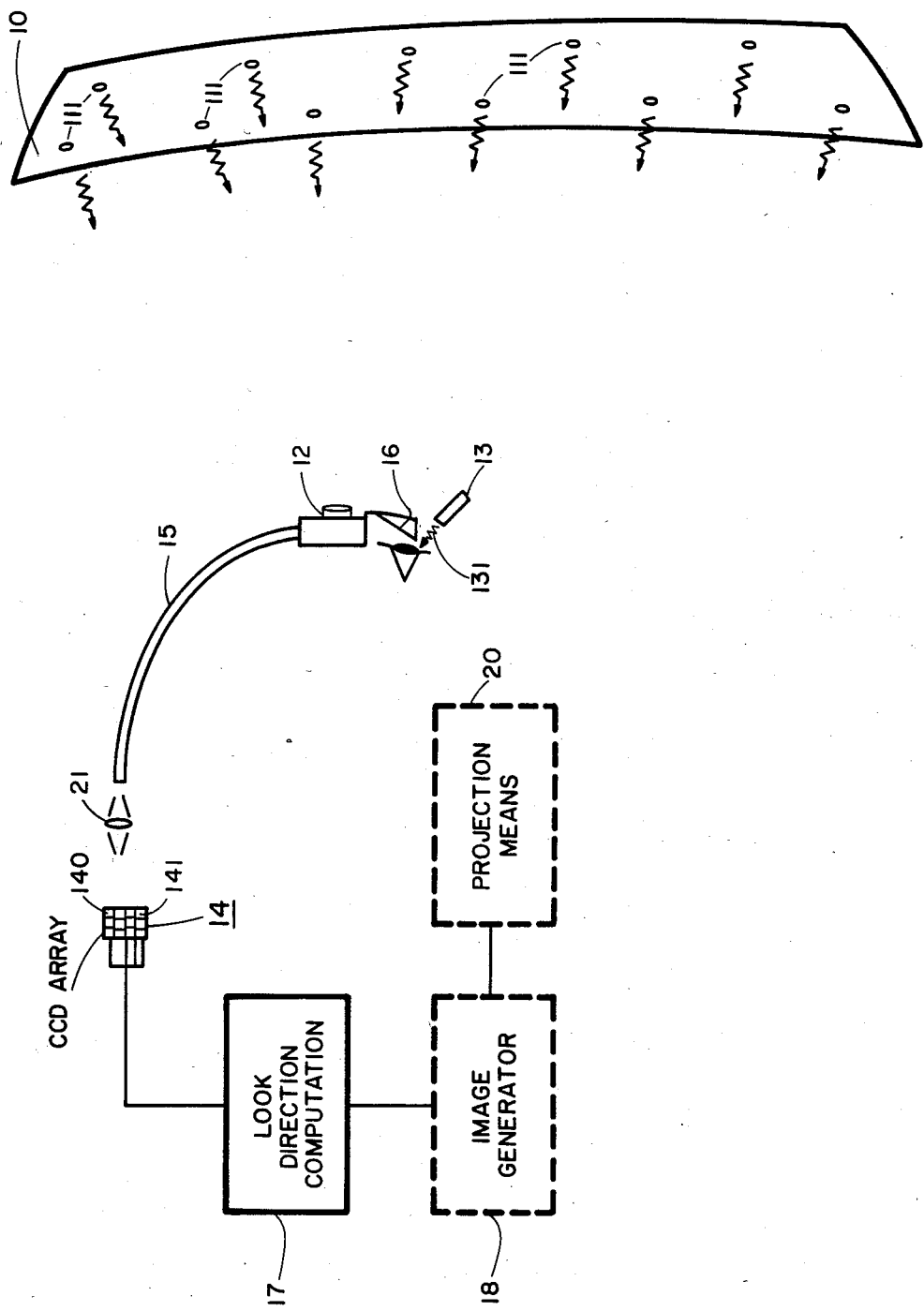

CCD HEAD AND EYE POSITION INDICATOR

BACKGROUND OF THE INVENTION

1. Field of the Invention

The present invention relates to the visual presentation of a simulator device. More particularly, the present invention relates to the detection and definition of the head and eye position of a person utilizing a vehicle simulator which provides a visual presentation of a view outside the vehicle. In even greater particularity, the invention may be described as a measurement device for inputting head and eye position data to a simulator from which a visual presentation in accordance with such data may be generated.

2. Description of the Prior Art

As the technology of flight simulation has progressed, the ability to more completely train aviators without the expenditure of costly fuel or aircraft time has experienced a concurrent rise. The internal cockpit simulation has long been a matter of duplication which provides the trainee with a transferred feeling of familiarity when he reaches the aircraft. To a degree, motion can be used to simulate the aircraft environment. The most dramatic and most difficult simulation is the outside the cockpit visual presentation.

Employed in this aspect of simulation have been a host of representations of the world as seen in flight, including everything from cartoonish films to TV cameras slaved to the trainee's head. Head position indicators have undergone their own evolution from direct measurement potentiometers attached to helmets to electronic field effect devices, to light beam and mirror systems. Generally the head position can be determined or the eye position can be determined, but to define the field of view of the trainee and concentrate the video presentation effort into that area, the knowledge of both head and eye position simultaneously and rapidly is required.

SUMMARY OF THE INVENTION

The present invention continues the evolution of simulator technology and adds thereto by the introduction of an innovative addition to the current art. A head and eye position indicating device is herein disclosed which utilizes an infrared light source reflected from the cornea of the eyes to yield eye position in accordance with the prior art; however, also provided are additional coded IR sources which are reflected and detected to determine head position. All of the IR reflections are transmitted via a fiber optic means to a charge coupled diode array which provides a very high speed conversion into electrical impulses indicative of the relative positions of the sources within the field of view of the trainee from which head and eye position can be computed.

It is an object of the present invention to provide a means for simultaneously tracking the head and eye movement of a subject.

Another object is to supply data on head and eye movement to a visual projection system for integration thereto.

Yet another object is to provide a rapid response head and eye tracker which can be used with a head slaved projector system to interface a trainee to a simulator having a visual display.

The foregoing and other objects, features, and advantages of the invention, and a better understanding of its construction and operation will become apparent from the following detailed description taken in conjunction with the accompanying drawings.

BRIEF DESCRIPTION OF THE DRAWINGS

The FIGURE is an expanded block diagram of the invention.

DESCRIPTION OF A PREFERRED EMBODIMENT

In a head slaved projection system, such as a helmet mounted projection system or an off the head projection system, the projection axis is basically fixed with respect to the head of the user. Thus as the head moves, so moves the projected scene. Obviously, as the scene follows the head movement it should change in accordance with the head orientation. If further refinements are made to the projected scene, such as inserting a highly detailed area of interest corresponding to the area at which the user's eyes are directed, then the eye and head orientation is required in order to present the proper scene. When inputting these positional parameters into an image generator 18 such as a Computer Image Generator (CIG) to display a simulated view, speed is also of the essence due to the processing time needed to model the appropriate image.

The current invention proposes the utilization of an array 11 of IR emitters 111 dispersed about the spherical dome 10 upon which the visual presentation is displayed. IR emitters 111 are coded such that each can be identified by its location on the dome. Differentiation between each of the emitters in array 11 can be accomplished by pulsing each of emitters 111 with an individual code, setting the intensity of each emitters at a different level, or spectrally varying the output of each emitter.

If the field of view of the user is restricted within reasonable limits, only a few of the emitters in array 11 will be visible at any given time. From the position of each visible emitter relative to the user and from the fixed position of each emitter the head orientation can be calculated. An imaging lens 12 which references the subject field of view is mounted to the users head along the facial center line, preferably above the eyes, without, however, interfering with the head motion. A separate IR source 13 is mounted near the dominant eye such that an IR spot 131 is reflected off the eyeball.

The area referenced by imaging lens 12 and encompassing several emitters from array 11 is transferred via a fiber optic bundle 15 to a remote charge coupled diode (CCD) array 14. IR spot 131 is reflected by a beam splitter 16, located in front of the eyes, along the optical path of fiber optic bundle 15 to CCD array 14, superimposing an indication of the eye position on the referenced area. The technique of reflecting a reticle or spot off the eye to indicate the position thereof is well known as is shown by the NAC Eye Mask Recorder, which also references an area of the field of view using an imaging lens.

The combined IR transmission is focused in CCD array 14 by focusing optics 21 such that each element of CCD array 14 corresponds to an area within the field of view referenced by lens 12. Thus each CCD 141 in array 14 receives in effect an element of the transmitted IR scene, thus each IR emitter 111 encompassed in the referenced area will be detected by a CCD 141 corresponding to the location of each emitter 111 in the referenced area. Each CCD 141 outputs an electrical signal corresponding to the coded IR emitter 111 or IR spot 131 to a computer system 17 which contains in its memory 171 the coordinates of each emitter in array 11. Computer system 17 may therefore rapidly calculate the orientation of the head and the axial displacement of the eyes from the data supplied via CCD array 14 and memory 171.

The speed of the data generation is enhanced by the use of a plurality of linear CCD arrays 140 making up CCD array 14. Each array 140 can be read out in less than 60 microseconds. Thus by reading out each array 140 simultaneously into a separate processing channel in computer system, 17, the entire image may be scanned in the 60 microsecond interval. The parallel processing of the IR image data is feasible as shown by the development of NASA's Massively Parallel Processor by Goodyear Aerospace Corporation, and such processing greatly increases the speed at which positioned data can be input into the associated image generator 18, although the system required is much smaller.

While a preferred embodiment has been shown and described, various modifications and substitutions may be made thereto without departing from the spirit and scope of the invention. Accordingly, it will be understood that the present invention has been described by way of illustration and not limitation.

What is claimed is:

1. An apparatus for head and eye tracking a live subject and generating positional outputs corresponding thereto, comprising in combination:
    a plurality of coded light emitters affixed to a projection area whereupon a visual presentation may be projected, each said emitter oriented to direct invisible light toward said subject and being distinctively coded one from the other so that each is separately identifiable by its output;
    optical means removably attached to the head of said subject for referencing a portion of said projection area encompassing less than all but more than two of said coded light emitters wherein said portion is fixed in size and correlated to the head orientation of said subject, and can vary in placement throughout said projection area;
    a light source of invisible light directed toward the eye of said subject such that said invisible light is reflected by said eye and said reflection indicates the position of the eye;
    charge coupled devices arranged in an array for detecting said individual light emitters and said source, said devices having a very high readout rate and outputs corresponding to detected said emitters and said source;
    a fiber optic bundle optically coupled to said referencing means and said light source for transferring said reflected light and said light from said referencing means to said detecting means;
    means for imaging said transferred light on said detecting means; and
    means for computing the spatial orientation of the head and eye outputting said computed data to control said visual presentation, operably connected to receive positional data from said detecting means.

2. An apparatus according to claim 1, wherein said plurality of coded light emitters is an array of IR emitters, each emitter having a distinctive code and a discrete location within said projection area.

3. An apparatus according to claim 1, wherein said referencing means comprises:
    an imaging lens for focusing light from said portion of said projection area into said fiber optic bundle for transferring said light; and
    means for mounting said lens on said subject along his facial centerline above his eyes.

4. The apparatus of claim 1, wherein said light source is an infrared source.

5. The apparatus of claim 1, wherein said array of charge coupled devices comprises:
    a plurality of sub-arrays of charge coupled devices; and
    means for simultaneous readout of data generated by said sub-arrays, operably connected between said sub-arrays and said computing means.

6. The apparatus of claim 1, further comprising a beam splitter supported by said apparatus at a position forward the eyes of said subject such that the reflection from said light source is coupled into said fiber optic bundle.

7. An apparatus for the rapid measurement of head and eye movements, for use in a training simulation which utilizes a helmet mounted projector to reflect computer generated images from a spherically domed screen surrounding the user, comprising in combination:
    a plurality of infrared emitters embedded within said screen such that IR light therefrom is incident upon the helmet of said user, each of said emitters being distinctly coded in accordance with its fixed position within said screen;
    an imaging lens mounted to said helmet referencing a portion of said screen which encompasses more than two but less than all of said IR emitters, wherein the position of said portion of said screen is correlated to the orientation of said helmet and can vary throughout said screen;
    means for directing an IR light source toward the eye of the user for reflecting therefrom such that said reflection is indicative of the position of the eye, cooperatively mounted on said helmet;
    a CCD array for detecting said IR radiation from said emitters and source, each CCD corresponding to a respective area on said screen, and said array having a very high readout rate, outputting an electronic signal in accordance with the emitters and source detected;
    fiber optic means for transferring light from said imaging lens to said CCD array;
    means for optically mating said fiber optic means to said CCD;
    means for optically superimposing said reflected IR light from said user at said fiber optic means onto said light from said emitters; and
    means coupled to said CCD array output for computing head and eye orientation.

* * * * *